United States Patent [19]

Yoshihara et al.

[11] Patent Number: 5,241,091
[45] Date of Patent: Aug. 31, 1993

[54] METHOD OF EXTRACTING A PHYSIOLOGICAL ACTIVE SUBSTANCE FROM THE HUSKS OF PINE NUTS AND ANTI-CONTAGION MEDICINE MADE OF SAID EXTRACT AS PRINCIPAL RAW MATERIAL

[75] Inventors: Masazumi Yoshihara, Hiroshima; Hiroshi Sakagami, Yokohama, both of Japan

[73] Assignee: Masazumi Yoshihara, Hiroshima, Japan

[21] Appl. No.: 754,161

[22] Filed: Sep. 3, 1991

Related U.S. Application Data

[63] Continuation of Ser. No. 378,232, Jul. 12, 1989, abandoned.

[30] Foreign Application Priority Data

Sep. 17, 1987 [JP] Japan .................................. 62-233472

[51] Int. Cl.$^5$ ................................................ C07C 1/00
[52] U.S. Cl. .......................................... 554/13; 554/9; 554/15; 554/17; 424/195.1
[58] Field of Search .................... 424/195.1; 554/9, 15, 554/13, 17

[56] References Cited

FOREIGN PATENT DOCUMENTS 0290026 12/1988 European Pat. Off. .
0463803 12/1988 European Pat. Off. .

OTHER PUBLICATIONS

Biological Abstracts, vol. 81, #12, p. 660, 113512, 1986.
Chemical Abstracts, vol. 95, p. 355, 1981, 58076g.
Biological Abstracts, vol. 88, #10, 1988, 103046.
Mukoyama et al., "Effect of Pine Seed Shell Extract on Rotavirus and Enterovirus Infections", Letters in Applied Microbiology, 1991, pp. 109–111.
Sakagami et al., "Effect of Pine Seed Extract on Microbial and Viral Infection", in vivo 6, 1991, pp. 13–16.
Sakagami Hiroshi et al., "Antitumor Activity of Polysaccharide Fractions from Pine Cone Extract of Pinus Parviflora Sieb et Zucc.", Anticancer Research 7: 1153–1160 (1987).
Atsushi Mukoyama et al., "Effect of pine seed shell extract on rotavirus and enterovirus infections", Food Research Laboratory, Australia (submitted to CSIRO for publication).

*Primary Examiner*—José G. Dees
*Assistant Examiner*—Deborah D. Carr
*Attorney, Agent, or Firm*—Cushman, Darby & Cushman

[57] ABSTRACT

The method of extracting a physiological active substance in which a granular acid polysaccharide is a principal component is disclosed. The husks of the pine nuts are immersed in an alkali solution to proceed an extraction treatment. The obtained extract is filtered and insoluble substances are separated and then remained solution is concentrated and arranged its degree of pH. Thus physiological active substance in which a granular acid polysaccharide is a principal component is extracted through lyophilization treatment. The anti-contagion medicine in which an acid polysaccharide obtained by the extraction method is a principal component provides with an activation function which by far surpasses an activation function of the polymorphonuclear leukocyte of conventional anti-tumor polysaccharides.

8 Claims, No Drawings

METHOD OF EXTRACTING A PHYSIOLOGICAL ACTIVE SUBSTANCE FROM THE HUSKS OF PINE NUTS AND ANTI-CONTAGION MEDICINE MADE OF SAID EXTRACT AS PRINCIPAL RAW MATERIAL

This is a continuation of application Ser. No. 07/378,232, filed on Jul. 12, 1989, which was abandoned upon the filing hereof.

BACKGROUND OF THE INVENTION

The present invention relates to a method of extracting a physiologically active acid polysaccharide from the husks of pine nuts such as black pine, red pine and white pine trees and an anti-contagion medicine in which the aforementioned extract is a principal raw material.

DESCRIPTION OF THE PRIOR ART

For many years, the pine nuts have been considered to be an edible nut of high nutritive value.

In particular, a pine nut oil extracted from the pine nuts has been evaluated as a nutritious component having physiological activity. Also in some districts pinecorns containing pine nuts therein have been evaluated by means of decoction for potential medical usage. In either case, it is well known that the pine nuts or the pinecorns contain some highly physiological active substances.

Assuming the aforementioned matters, the inventors of the present invention have carried out the development and research work in order to enlarge the scope of utilization of the pine nuts as well as the pinecorns. For instance, techniques to extract oil from pine nuts and techniques to extract the pine nuts from the firm husks of the pine nuts have been developed.

Extraction of pine nut oil resulted in a residue in the form of a pressed cake. To obtain the residue the husks are removed from the pine nuts and are decocted by means of boiling water (known as hot water extraction). The solution obtained by the extraction treatment undergoes paper filtration and is concentrated. As a result of this experiment the inventors found a polysaccharide which has a remarkably high physiological activity. Particular an activation function of granulocyte in a white blood corpuscle, is a great importance.

SUMMARY OF THE INVENTION

It is an object of the present invention to efficiently extract from pine nut husks an acid polysaccharide with a remarkable activation function. For this purpose the husks of pine nuts are treated by fat removal treatment immersed in an alkali solution for proceeding alkali solution extract treatment and then the pH of the extracted solution is adjusted. The extracted solution is treated by a centrifugal separator and an extract is precipitated. The precipitated extract is concentrated by means of filtration treatment. The concentrated extract solution is made into a granular acid polysaccharide after lyophilization. Thus an essence contained in the husks of pine nuts is extracted and recovered.

In other words, the present invention is characterized in that the fats and other lower polymer substances are removed from the husks of the pine nuts are removed by means of fat removal treatment. Then, alkali solution is added for proceeding an extraction. An extract solution obtained after extracting treatment is adjusted to have a certain pH. Thus an acid polysaccharide is extracted and recovered from the husks of the pine nuts.

As a result of various experiments, it was shown that the white pine nuts are the most preferable ones surpassing other black and red pine nuts for the purpose of the present invention.

It was also shown that the husks of the white pine nuts deforestated in the middle of November is most preferable.

The husks of the pine nuts are solid and heretofore it has been difficult to remove the husks efficiently from the pine nuts. However, the inventors have successfully invented a device including a breaking and crushing means and, as a result, removing the husks from the pine nuts is much easier. It was also shown that if the husks separated from the nuts are dried, and they are crushed to a degree suitable for extraction, the working efficiency of the present invention is greatly improved.

The alkali solution which is used in the extraction treatment of the present invention is selected from either an alkali solution of organic chlorite or inorganic chlorite. However, taking into consideration after-treatments of the extracted solution and extracted substance, ammonia water which can remove alkali by heat treatment is considered to be most preferable.

A degree of alkalization of the alkali solution depends upon the sort of contents of the pine nuts. It was shown that an alkalization degree of pH 7 or over is desirable, and preferably, a degree between pH 7.5 to 10 is most desirable.

The extraction work of the present invention is started from a process of immersing the pine nuts, which were broken and crushed to a desirable size, into an alkali solution.

The amount of alkali solution to be used for extraction is not particularly limited but it is preferable to use an amount as much as five times the pine nuts. The alkali solution of ordinary temperature is used but the alkali solution of high temperature can also be used.

The extracted solution is separated from the pine nuts by means of filtration treatment or the like, and it is concentrated to a proper degree of concentration by means of decompression, concentration, or the like. Then the pH is adjusted by means of a proper acid such as hydrochloric acid or the like. Finally a granular type acid polysaccharide is recovered through final lyophilization.

The granules of acid polysaccharide obtained and recovered by a process of the present invention have a distinct smell. The granules are brown in color and are easily dissolved by water.

DETAILED DESCRIPTION OF THE PREFERRED EMBODIMENTS

The extraction method of acid polysaccharide is explained on the basis of the following preferred embodiments:

The pine nuts of the white pin tree collected at Konchianshi of Chiirin-sho in the People's Republic of China in the middle of November are prepared for treatment.

As a pretreatment of a process of the present invention, 1 kg of the husks of the pine nuts are washed with about four liters methanol solution. Oils and fats and lower polymer substances contained in the pine nuts are removed.

Next, the pine nuts washed in the above pretreatment are immersed in about four liters of boiling water. This hot water extracting treatment is repeated three times, each for six hours. The obtained crude extracted solution is filtered by paper filters and insoluble substances are removed. The obtained extracted solution is concentrated under the decompressed condition. The obtained concentrated solution is diluted with ethanol as much as six times the amount of the concentrated solution. The obtained precipitate is dissolved by distilled water, then lower polymer substances are removed through dialysis treatment, and finally the so-called hot water extract is recovered.

Further, six liters ammonia water of 0.8% conc. is added to the residue remaining after hot water extraction treatment, and the mixture is stirred for three hours at 45° C. after which the extracted liquid is separated. The residue is again treated by extraction with ammonia water. Both the first and the second extracted solutions are mixed together and filtered by filter cloth.

Next, the filtered solution of 9.5 liters is concentrated to 150 ml at 40° C. under the decompressed condition. The pH of the filtered solution is adjusted to pH 5.4 by means of hydrochloric acid treatment and lyophilization. The brown granules of 4.5 grams of acid polysaccharide are obtained.

The granules obtained in the above extraction treatment have a smell which is distinct and one percent (W/V) solution thereof showed the degree of pH of 4.5-6.0.

The contents of arsenic and heavy metals in the granules of one gram are measured. The result showed the contents of less than two ppm and thirty ppm, respectively. A group of colon bacilli are atonic and the number of general germs is less than 1000/g.

The following diagram shows an extraction treatment of the present invention.

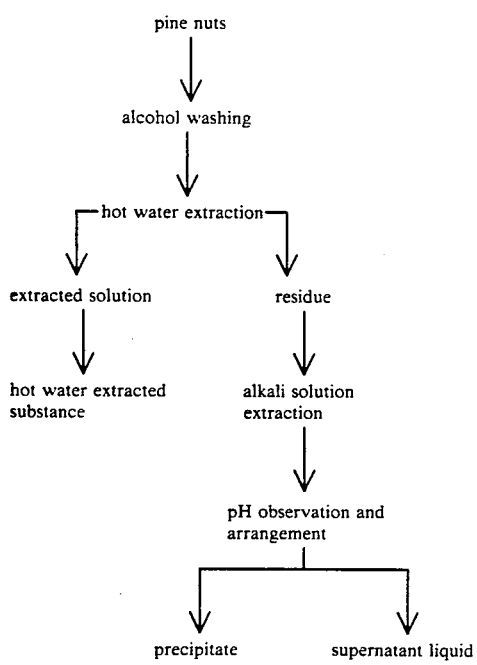

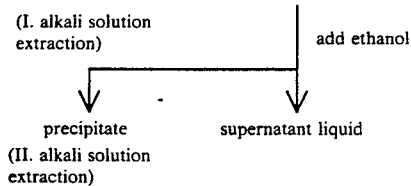

A testing of the activation function of the extracted acid polysaccharide is as follows:

In order to confirm a physiological activation function of the acid polysaccharide obtained by alkali solution extraction, the following method and arrangement are applied.

First, a human peripheral blood as a target germ for testing activation function is diluted to double quantity with physiological saline solution. The diluted solution is piled on the layer of Ficoll-Hypague (specific gravity is 1.077) and treated with a centrifugal separator for thirty minutes at 1,500 rpm. The red corpsucal and polymorphonuclear leukocyte fraction are taken out from the lower layer of the mixture.

The red corpsucal and polymorphonuclear leukocyte fraction are washed with physiological saline solution and diluted with blood serums prepared in the first centrifugal separator treatment. The obtained diluted mixture is piled on the layer of Mono-Poly Resolving Medium Ficoll-Hypague (specific gravity is 1.114) and treated with the centrifugal separator for thirty minutes at 1,500 rpm. The intermediate layer comprising polymorphonuclear leukocyte is collected. Next, said intermediate layer is washed twice with a culture fluid of RPMI 1640 of non-blood serum and purified polymorphonuclear leukocyte fraction is obtained as a target germ. The purity of the polymorphonuclear leukocyte is more than 95%.

The target germ obtained on the basis of the foregoing treatments is added with hot water extracted polysaccharide in the Table - I as well as extracted acid polysaccharide I and II by alkali solution to confirm its physiological activation function. As a method of confirmation, Klebanoff and Clark's method (J. Lab. Clin. Med. 89:675-686, 1977) was applied after being slightly revised.

Namely, the polymorphonuclear leukocyte of $1 \times 10^6$ pcs. are suspended in the culture fluid of 0.5 ml of non-serum RPMI 1640, said culture fluid containing the substances to be tested of various kinds of concentration (hot water extracted polysaccharide, alkali solution extracted acid polysaccharide I and II, and TAK, CM-TAK for comparison) as well as $8 \times 10^{-6}$ M radioactivity $Na^{125}$ I (I uCi/ml). An incubation treatment of one hour is carried out at a temperature of 37° C., followed by a washing with physiological saline solution. Then, iced 5% trichloro acetic acid is added. It is left in an ice bath for twenty minutes, then treated with a centrifugal separator for ten minutes at 3,000 rpm and radioactivity existing in the precipitate (acid insoluble fraction) is measured with gamma-ray counter.

TABLE I

Activity function of polymorphonuclear leukocyte of human peripheral blood by acid polysaccharide extracted from husks of pine nuts.

| kind | extract | conc. ($\mu$g/ml) | radioactive iodiene taken into acid insoluble fraction of polymorphonuclear leukocyte (pmol/$10^7$ cells/hr) polymorph. |
|---|---|---|---|
| husks of pine nuts | hot water extract polysaccharide | 100<br>1000 | 231<br>460 |
| husks of pine nuts | alkali solution extract polysaccharide I | 100<br>1000 | 451<br>279 |
| husks of pine nuts | alkali solution extract polysaccharide II | 100<br>1000 | 242<br>369 |
| TAK | | 100<br>1000 | 32<br>89 |
| CM-TAK | | 100<br>1000 | 6<br>7 |
| physiological solution for comparison | | —<br>— | 7<br>9 |

Remarks: (1) TAK, CM-TAK are anti tumour polysaccharide developed in Japan providing with the strongest activity function.
Remarks: (2) TAK ... (1 → 3) - beta - D - glucan) (Cancer Res 38, 379-383, 1987) isolated from Alcalignes faecalis var. myxogenes (IFO 13140).
CM-TAK ... (Carboxy-methylised TAK) (Europ. J. Cancer. 15, 211-215, 1979).

As shown in the Table - I, the acid polysaccharide obtained from alkali solution extraction method of the present invention activates polymorphonuclear leukocyte strongly, and it was shown that the acid polysaccharide obtained from the present invention can provide an activation function by surpassing T A K, C M - T A K which have been considered to be the strongest of the currently existing anti-tumor polysaccharides in Japan.

Next, in order to provide an anti-contagion medicine in which granules of said acid polysaccharide obtained from the aforementioned treatments is used as principal raw material the following processes of (1) and (2) are applied.

(1) The pine nuts oil is added to 2 mgs of granules of acid polysaccharide, then gelatinized and made a capsul tablet. (2) 10 grams of the acid polysaccharide are added to approximately 85 ml of water and stirred and dissolved for thirty minutes at temperature between 50°-60° C. Next, 0.7 gram salt and water is added dissolved solution and 100 ml solution was prepared.

Then the solution was treated by a centrifugal separator for twenty minutes at 10,000 rpm. Insoluble substances are removed and sterilized in a high pressure autoclave. Finally, a sterilized ampul injection is obtained.

Next, the activity of the anti-contagion medicine obtained from the aforementioned treatments is observed by the following testing method.

For measuring the activity of the anti-contagion medicine of the acid polysaccharide the following (1) and (2) testings are applied.

(1) Effectiveness testing against an infection of colon bacilli:

The granules of 0.25 mg or the physiological saline solution is prescribed for ddy mice (five-week year, male), each group comprising ten to twelve mice. On the second day colon bacilli drug of $4 \times 10^6$ are transplanted into abdomen of the mice and the number of surviving mice is counted after twenty four hours.

(2) Effectiveness testing against viral infectious disease:

10 mg/kg of said infection liquid is injected the designated times in the muscle of the thigh or in the middle part of the scapula of backbone of dogs and cats infected with viral disease, and change with the passage of time of general status and the number of white blood corpuscle in the blood is observed.

Obstruction activity against infection of colon bacilli in mice and relaxation status of disease of cats suffering from viral disease are taken as indexes and working effects of anti-contagion medicine is observed. The results are as follows:

(1) Effectiveness against infection of colon bacilli:

As shown in the Table - II, if abdomens of mice are previously treated with ammonia solution extract, said extract containing granules that are dissolved in the physiological saline solution, infection of colon bacilli was remarkably inhibited.

TABLE II

Defend-effect of ammonia water extract of pine nuts (granular acid polysaccharide) against colon bacilli infection.

| medicine | number of mice alive after five days |
|---|---|
| alkali solution extract of pine nuts | |
| I | 7/10 (70%) |
| II | 5/10 (50%) |
| physiological saline solution for comparison | 1/12 (8%) |

(2) Effectiveness against infection of viral disease:

Ammonia water extract of the husks of pine nuts is hypodermically injected near the scapula of backbone or intermuscularly injected into the femoral region of cats and dogs. As a result viral diseases such as Calici viral glossitis, stomatitis; toothtis, Parvo viral cats leukopenia and Herpes viral nose-bronchitis are greatly inhibited, promoting appetite, and improving general status. Some of the animals fully recovered from the disease. To the contrary, the medicine was ineffective against disease such as mammary cancer or fibrous salcoma that the virus does not cause. Table - III shows results against viral diseases.

TABLE III

Defend-effect of acid polysaccharide (injection) extracted from pine nuts against viral disease.

| animal | year month | m. or f. | name of disease | status | amount mg/kg | method | result |
|---|---|---|---|---|---|---|---|
| cat | 2 | f. | Calici viral infection | cough, sneeze | 10 | H × 2 | + relaxation |
| | 2 | f. | Calici viral infection | stomatitis | 10 | H × 2 | + relaxation |
| | 2 | f. | Calici viral infection | snivel | 10 | H × 2 | + relaxation |
| | 2 | f. | Calici viral infection | fever | 10 | H × 2 | + relaxation |
| | 2 | m. | Calici viral | no appetite | 10 | H × 1 | + + + fully recovered |

TABLE III-continued

Defend-effect of acid polysaccharide (injection) extracted from pine nuts against viral disease.

| animal | year month | m. or f. | name of disease | status | amount mg/kg | method | result | |
|---|---|---|---|---|---|---|---|---|
| | 12 | m. | Calici viral infection | glossitis | 10 | M × 3 | ++ | recovered after 24 hrs. |
| | 12 | m. | Calici viral infection | glossitis | 10 | M × 3 | ++ | recovered |
| | 2 | f. | Herpes viral bronchitis | cough, sneeze, nasitis, fever | 10 | M × 2 | ++ | recovered |
| | 2 | f. | Herpes viral bronchitis | snivel | 40 | H × 1 | ++ | recovered |
| | 12 | m. | Herpes viral bronchitis | gum | 10 | M × 2 | ++ | recovered |
| | 3 | m. | Parvo viral leukocytepenia | leukocytepenia, vomiting | 10 | M × 2 | ++ | recovered incre. corpuscle |
| dog | 2 | m. | Parvo viral leukocytepenia | leukocytepenia, vomiting | 10 | H × 2 | +++ | fully recovered after 24 hrs. |
| cat | 72 | m. | fibrous cancer | | 10 | M × 15 | − | no effect |
| dog | 12 | f. | mammary cancer | | 10 | H × 2 | − | no effect | m.: male
f.: female
H.: hypodermic injection
M.: muscle injection

As aforementioned, a present invention relates to the method of extracting an acid polysaccharide of high activity from the husks of pine nuts. The inventors successfully developed an effective scope of utilization of the extract. The method presents the following technical advantage.

(1) It became possible to extract a substance of high physiological activity from the husks of pine nuts which have so far been neglected.

(2) Alkali solution is used as a means of extraction. It is therefore possible to repeat the means without trouble and accordingly a valuable component is effectively extracted.

(3) The substance extracted and recovered by the present invention is an acid polysaccharide that has an activation function of polymorphonuclear leukocyte. This kind of acid polysaccharide has not been heretofore used as a substance which promotes activity of polymorphonuclear leukocyte. The polymorphonuclear leukocyte has a function to defend infection. It is also possible that the invention can be used as medicine, making use of its activity promotion function.

In particular, as in aforementioned experiments, infection of colon bacilli to mice is inhibited and viral disease of cats and dogs is effectively controlled.

Furthermore, as the anti-contagion medicine of the present invention is extracted and recovered from the husks of natural pine nuts, it does not produce any strong adverse effects which have been seen in other anti-virus drug. It is also possible to combine it with other curative means or anti-virus drug to effectively cure various viral diseases.

what is claimed is:

1. A method of extracting acid polysaccharide from husks of pine nuts comprising:
   i) extracting said husks in an alkali solution;
   ii) adjusting pH of extraction solution;
   iii) precipitating extraction solution; and
   iv) separating insoluble substances from extraction to obtain acid polysaccharide.

2. The method according to claim 1, wherein said separating insoluble substances from extraction further comprises concentrating said extraction solution and adjusting the pH of solution to 5.4.

3. The method according to claim 2, wherein adjustment of pH to 5.4 is effected by treating with hydrochloric acid and lyophilizing.

4. The method according to claim 1 wherein said separating insoluble substances from extraction, further comprises removing lower polymer substances by dialysis treatment.

5. The method according to claim 1 where extracting husks in an alkali solution is preceded by hot water extraction.

6. An anti-viral and anti-bacterial composition comprising granular acid polysaccharide extracted by the method of claim 1.

7. A method of extracting a physiologically active substance comprising a granular acid polysaccharide component as principal raw material, said granular acid polysaccharide component being obtained by extraction from husks of pine nuts, the extraction method comprising:
   removing husks from the pine nuts by means of shell cracking apparatus;
   immersing the husks in an alkali solution of pH 7.5 to 10, amount of said alkali solution being five times that of said husks;
   extracting the husks by treatment by alkali solution;
   adjusting with diluted hydrochloric acid the pH of extracted solution;
   precipitating extract by means of centrifugal separator;
   separating any insoluble substance from said extract by filtration treatment;
   concentrating said extract;
   dialyzing with an amount of ethanol six times the amount of said concentrate, where the pH of said concentrate is adjusted with diluted hydrochloric acid to a pH value of 5.4;
   and lyophilizing to obtain said granular acid polysaccharide component.

8. An anti-viral and anti-bacterial composition comprising granular acid polysaccharide extracted by the method of claim 7.

* * * * *